(12) United States Patent
Hartwig

(10) Patent No.: US 9,040,751 B2
(45) Date of Patent: May 26, 2015

(54) METHOD FOR PRODUCING RING-HALOGENATED N,N-DIALKYLBENZYLAMINES

(75) Inventor: Jordan Hartwig, Bergisch Gladbach (DE)

(73) Assignee: LANXESS DEUTSCHLAND GMBH, Cologne, DE (US)

( * ) Notice: Subject to any disclaimer, the term of this patent is extended or adjusted under 35 U.S.C. 154(b) by 0 days.

(21) Appl. No.: 14/236,163

(22) PCT Filed: Aug. 1, 2012

(86) PCT No.: PCT/EP2012/064993
§ 371 (c)(1),
(2), (4) Date: Apr. 11, 2014

(87) PCT Pub. No.: WO2013/017611
PCT Pub. Date: Feb. 7, 2013

(65) Prior Publication Data
US 2014/0221691 A1    Aug. 7, 2014

(30) Foreign Application Priority Data
Aug. 4, 2011 (EP) .................................. 11176506

(51) Int. Cl.
*C07C 209/00* (2006.01)
*C07C 209/10* (2006.01)
*C07C 209/08* (2006.01)
*C07C 221/00* (2006.01)

(52) U.S. Cl.
CPC .............. *C07C 209/10* (2013.01); *C07C 209/08* (2013.01); *C07C 221/00* (2013.01)

(58) Field of Classification Search
CPC .................................................... C07C 209/10

USPC ......................................................... 564/405
See application file for complete search history.

(56) References Cited

FOREIGN PATENT DOCUMENTS

DE         676331          6/1939
JP    2003026640 A   *   1/2003

OTHER PUBLICATIONS

Bhattacharyya, "A High Throughput Synthesis of N, N-Dimethyl Tertiary Amines", Synthetic Communications, 30 (11), 2001-2008 (2000).
Pine et al., "The Base-Promoted Rearrangements of a-Arylneopentylammonium Salts", J. Org. Chem. vol. 36, No. 7, 1971.
Braun et al., "Adhesion Organiseher Residues, V. 1", Abstract translation (translate.google.com Sep. 15, 2014); (1926) Haftfestigkeit organischer Reste. V. Justus Liebigs Ann. Chem, 449: 249-277.
Short et al., "Sympathetic nervous system blocking agents. Investigation of ethyl-, hydroxyethyl-, vinyloxyethyl-, and propargyl-benzyldimethylammonium halides and related compounds", (1962), J. Pharm Sci., vol. 51, Issue 9, pp. 881-884.
Eliel et al., "Reactions of Esters with Tertiary Amines, II. The Reaction of Substituted Beyzyldimethylamines and Otehr Amines", the Chemical Laboratories of the University of Notre Dame and of Mercyhurst College, Jun. 8, 1954, pp. 1693-1697, Notre Dame, Indiana and Erie, Pennsylvania.
Singh et al., "Aqueous-Mediated N-Alkylation of Amines", Eur. Jo. Org. Chem., 2007, 1369-1377, 2007 Wiley-VCH Verlag GmbH & Co., KgaA, Weinheim, Germany.
International Search Report from International Application PCT/EP2012/064993 dated Oct. 11, 2012, 2 pages.

* cited by examiner

*Primary Examiner* — Sudhakar Katakam

(57) ABSTRACT

The invention relates to a method for preparing ring-halogenated N,N-dialkylbenzylamines and intermediates obtainable therefrom for preparing agrochemicals and pharmaceutically active ingredients.

10 Claims, No Drawings

METHOD FOR PRODUCING RING-HALOGENATED N,N-DIALKYLBENZYLAMINES

The invention relates to a method for preparing ring-halogenated N,N-dialkylbenzylamines and intermediates obtainable therefrom for preparing agrochemicals and pharmaceutically active ingredients.

Ring-halogenated N,N-dialkylbenzylamines are useful intermediates in methods for preparing agrochemicals and pharmaceutically active ingredients, since they enable, by metalation, such as lithiation or conversion to Grignard reagents, a further substitution on the aromatic ring by reaction, for example, with oxalic esters.

JP 2003 026640 A describes, for example, the conversion of 2-chloro-N,N-dialkylbenzylamines with magnesium and ethyl bromide in toluene and THF initially to 2-(butoxycarbonylcarbonyl)-N,N-dialkylbenzylamines, which in turn may be used for preparing certain fungicides of the strobilurin type such as kresoxim-methyl.

The preparation of the ring-halogenated N,N-dialkylbenzylamines used as starting materials is generally known. S. Bhattacharyya, Synth. Commun. 2000, 30, 2001-2008 describes the reaction of 2-chlorobenzaldehyde with dimethylamine to give the corresponding iminium salt and the subsequent reduction with sodium borohydride to the target product.

A Leuckart-Wallach reaction of 2-chlorobenzylamine with formaldehyde and formic acid is described in S. H. Pine et al., J. Org. Chem., 1971, 36, 984-991.

Braun et al, in Liebigs Ann. Chem. 1926, 449, 249-277 describe the reaction of o-chlorobenzyl chloride with dimethylamine in a sealed tube at 100° C. Details of the ratio of the two components and of the workup are not given. The disadvantage of this method, however, is that the resulting dimethylamine hydrochloride byproduct occurs in crystalline form and must be laboriously removed from the 2-chloro-N,N-dimethylbenzylamine.

A further method is described by J. H. Short et al., J. Pharm. Sci. 1962, 51, 881-884, which refers to the synthetic method of E. L. Eliel et al. (J. Org. Chem. 1954, 19, 1693-1698). In this case, benzene is saturated with gaseous dimethylamine and is reacted at room temperature with o-chlorobenzyl chloride at atmospheric pressure. Apart from the inconvenience of the required solvent removal, this method has the distinct disadvantage that only unfavorable reactant ratios can be achieved by the non-pressurized procedure, which promotes the formation of undesirable quaternary ammonium salts, particularly at the low reaction temperature.

DE 676331 recommends the reaction of o-chlorobenzyl chloride with dimethylamine and the removal of the resulting dimethylamine hydrochloride as a melt at high temperatures.

A common aspect of all the aforementioned synthetic methods is that they generate undesired byproducts; in syntheses starting from dimethylamine with o-chlorobenzyl chloride, in particular the occurrence of o-chlorobenzaldehyde as secondary component is observed.

Since this component has a very similar boiling point to the 2-chloro-N,N-dimethylbenzylamine target product, they cannot be effectively separated by distillation and said component interferes to a massive extent in subsequent reactions, particularly in metalation reactions.

Furthermore, particularly in commercially available 2-chlorobenzyl chloride, which is typically obtained by radical chlorination of 2-chlorotoluene, 2-chlorobenzal chloride is also frequently observed as impurity, which interferes with the amination.

Therefore, there is a need for a method which can be carried out on an industrial scale and which affords high yields and which also preferably allows the preparation of ring-halogenated N,N-dialkylbenzylamines having a content of 500 ppm or less, based on weight, of the corresponding ring-halogenated benzaldehydes.

A method for preparing compounds of the formula (I) has now been found

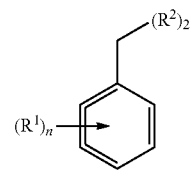

(I)

in which
n is 0, 1, 2 or 3, preferably 1 or 2, particularly preferably 1
the residues $R^1$ are each independently a halogen atom, preferably chlorine or bromine, more preferably chlorine, which is bonded to the aromatic ring
the residues $R^2$ are each independently $C_1$-$C_8$-alkyl, $C_6$-$C_{12}$-aryl or $C_7$-$C_{13}$-arylalkyl or both residues $R^2$ together are a straight-chain or branched $C_3$-$C_{12}$-alkylene residue, which may optionally be interspersed by one or more oxygen atoms
by reacting compounds of the formula (II)

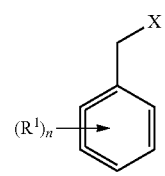

(II)

with compounds of the formula (III)

$HN(R^2)_2$ (III)

where the residues $R^1$, $R^2$ and $R^3$ in the formulae (I) and (II) have the meanings stated under the formula (I) and
X is chlorine, bromine, iodine, —$OSO_2$—($C_1$-$C_6$-alkyl) or —$OSO_2$—($C_1$-$C_6$-perfluoroalkyl), preferably chlorine or bromine, especially preferably chlorine
wherein the method is characterized in that
the molar ratio of compounds of the formula (III) to compounds of the formula (II) is 3:1 or greater, preferably 3:1 to 50:1, particularly preferably 3:1 to 20:1 and especially preferably 5:1 to 20:1 and also in another embodiment 5:1 or greater, preferably 5:1 to 50:1, particularly preferably 5:1 to 20:1 and especially preferably 8:1 to 14:1
organic solvent is used in an amount of 10% by weight or less, preferably 5% by weight or less, particularly preferably 0 to 2% by weight, based on the sum of compounds of the formulae (II) and (III) used and especially preferably no organic solvent is used and
water is used, preferably more than 10% by weight, preferably more than 30% by weight, especially preferably more than 50% by weight and particularly more than 100% by weight of water, preferably 100 to 1000% by weight, based on the compound of the formula (II) used.

In the context of the invention, the residue definitions or elucidations, listed in general terms or in the preferred ranges specified, may be combined with one another in any way and also, therefore, between the respective ranges and preferred ranges.

Both residues in the compounds of the formulae (I) and (II) $R^2$ are each preferably independently, each particularly preferably identically, $C_1$-$C_8$-alkyl or combined are a straight-chain or branched $C_5$-$C_6$-alkylene residue or an ethanediyl-oxo-ethanediyl residue each especially preferably identically methyl, ethyl, n-propyl, n-butyl, 1,4-butanediyl or 1,5-pentanediyl, wherein methyl and ethyl is further preferred and methyl still further preferred.

For cases in which n=1
the residue $R^1$ is preferably a chlorine or bromine residue ortho to the benzyl group, preferably an ortho chlorine residue A particularly preferred compound of the formula (I) is 2-chloro-N,N-dimethylbenzylamine.

A particularly preferred compound of the formula (II) is 2-chlorobenzyl chloride.

A particularly preferred compound of the formula (III) is dimethylamine.

The reaction temperature is, for example, between 50 and 200° C., preferably between 90 and 180° C., especially preferably 130 to 150° C.

The reaction pressure typically depends heavily on the vapor pressure of the compound of the formula (III) used and the vapor pressure of the water at the reaction temperature and may be, for example, 2 to 300 bar, preferably 4 to 50 bar and particularly preferably 5 to 35 bar. In the examples, the pressure was adjusted to values between 8 and 31 bar.

The reaction time is typically between 5 min and 24 hours and preferably between 30 min and 5 hours. Longer reaction times are not detrimental but have no added advantage.

The excess compound of the formula (III) may be recovered for recycling into the reaction, for example, in a manner known per se by thermal treatment, ideally by pressure distillation.

In the reaction, the corresponding hydrohalides of the compounds of the formula (III) are also formed, which are present at least partially, preferably completely, dissolved in water and which can also be liberated in a manner known per se by addition of base and be recovered. Suitable bases for this purpose are particularly alkali metal and alkaline earth metal carbonates and hydroxides such as sodium, potassium and calcium hydroxide or carbonate; preference is given to sodium hydroxide.

The method may be carried out both in batchwise and continuous mode, although the continuous procedure is preferred.

For the continuous procedure, for example, a tubular reactor may be used into which the feedstocks are pumped. After passing through the delay zone, the reaction mixture pressure is reduced and the excess compound of the formula (III) is recovered in a pressure distillation.

The further workup can then be conducted, for example, in a batch process, in which case the treatment with base can be conducted in a mixer settler apparatus for example.

The aqueous phase is separated from the organic phase, which contains the product or is formed by the product, and the organic phase is then purified, preferably by distillation. The reaction with base described above may be conducted before or after removal of the aqueous phase.

The compounds of the formula (I) according to the invention are obtained in excellent yields of over 92%, in some cases over 95%, of theory. Purities of up to 99.9% by weight are obtained following distillation.

Surprisingly, it has further been found that the compounds of the formula (I) can be freed from residual contents of benzaldehydes by reacting, in a further step,
compounds of the formula (I), having a content of compounds of the formula (IV)

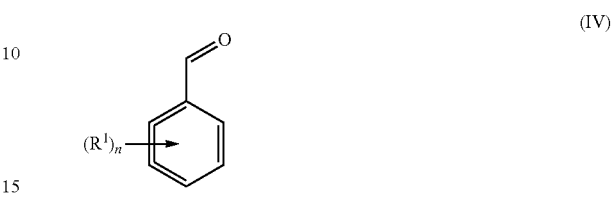

of preferably 0.050 to 2.0% by weight, particularly preferably 0.1 to 1.0% by weight, with an alkali metal borohydride or an alkali metal aluminum hydride and then optionally, though preferably, by carrying out distillation.

Preferred alkali metal borohydrides are lithium borohydride and sodium borohydride and a preferred alkali metal aluminum hydride is lithium aluminum hydride $LiAlH_4$.

The addition of sodium borohydride is preferred.

A particularly preferred compound of the formula (IV) is 2-chlorobenzaldehyde, which occurs in the preparation of 2-chloro-N,N-dimethylbenzylamine.

The amount used can be, for example, between 0.01 and 5% by weight, preferably between 0.02 and 2% by weight, particularly preferably between 0.02 and 0.4% by weight, based on the weight of the compound of the formula (I) used having a content of compound of the formula (IV).

The reaction temperature in this case is, for example, at 0 and 150° C., preferably at 15 and 100° C., especially preferably at 40 to 80° C.

The reaction time is typically between 5 min and 24 hours, preferably between 30 min and 5 hours.

Longer reaction times or higher amounts of alkali metal borohydrides or aluminum hydrides are not detrimental but confer no added advantage.

The completion of the reaction can be monitored, for example, by HPLC.

The compounds obtained according to the invention have a content of corresponding benzaldehydes of typically less than 50%, preferably less than 70%, of the original amount.

The advantage of the invention lies in the efficient preparation of high purity compounds of the formula (I), which are free from secondary components such that they can be used particularly in metalation reactions such as Grignard reactions.

From the invention, therefore, is the use of the compounds of the formula (I) prepared according to the invention in metalation reactions and also a method for preparing compounds of the formula (V)

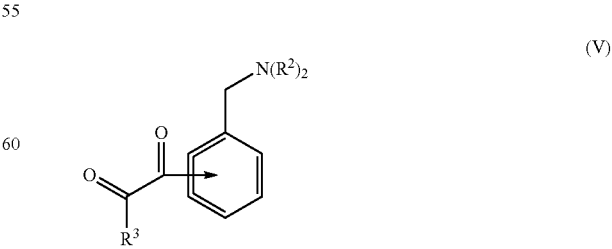

in which the residues $R^2$ have the meaning stated above, including the preferred ranges thereof, and $R^3$ is $C_1$-$C_8$-alkyl, $C_1$-$C_8$-alkoxy, $C_6$-$C_{12}$-aryl or $C_7$-$C_{13}$-arylalkyl, characterized in that the compounds of the formula (I) prepared according to the invention are reacted initially with an alkali metal or alkaline earth metal or a compound of the type $M(C_1$-$C_6$-alkyl), where M is an alkali metal and subsequently with compounds of the formula (VI)

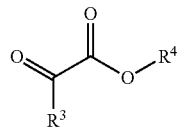

in which the residue $R^3$ has the meaning stated for formula (V) and
$R^4$ is $C_1$-$C_8$-alkyl, $C_6$-$C_{12}$-aryl or $C_7$-$C_{13}$-arylalkyl.

The reaction of the compounds of the formula (I) is preferably conducted initially with magnesium and then with oxalic di($C_1$-$C_8$-alkyl) esters.

EXAMPLES

Example 1

An autoclave was charged with 114.4 parts by weight of 99.7% o-chlorobenzyl chloride and 176 parts by weight of water. 156.8 parts by weight of dimethylamine were then condensed in. The mixture was heated with stirring to 140° C. and then stirred at this temperature for 30 min. The pressure was adjusted to ca. 1.5 MPa. The mixture was then allowed to cool to room temperature and depressurized. The mixture was then purged with nitrogen for 30 min to remove excess dimethylamine. After transferring to a laboratory reactor, the mixture was heated with stirring at 90° C. for 3 h, during which further dimethylamine was expelled. At the same temperature, 117.4 parts by weight of 50% by weight aqueous sodium hydroxide solution was added in order to liberate the organic bases. The mixture was stirred for 1 h at 90° C., allowed to settle out and the phases were separated.

The organic phase was distilled by means of a column at a reduced pressure of 14 mbar. A water-containing forerun was removed which was reused in the reaction according to this example.

| Forerun: | bp = 84° C. | 24.9 parts by weight | purity: 99.3% |
| Main fraction: | bp = 84° C. | 87.7 parts by weight | purity: 99.2% |

According to HPLC, the main fraction did not contain any detectable proportions of bis(2-chlorobenzyl)dimethylammonium chloride and 2-chlorobenzal chloride.

The sum of the 2 fractions corresponded to a chemical yield of 93.0% of theory.

Example 2

Analogously to example 1, 76.24 parts by weight of o-chlorobenzyl chloride and 117.4 parts by weight of water were reacted with 228.2 parts by weight of dimethylamine at 110° C.

After aqueous workup as in example 1 and distillation at 14 mbar, the following fractions were obtained:

| Forerun: | bp = 84° C. | 0.76 parts by weight | purity: 99.0% |
| Main fraction: | bp = 84° C. | 73.3 parts by weight | purity: 99.7% |

According to HPLC, the main fraction did not contain any detectable proportions of bis(2-chlorobenzyl)dimethylammonium chloride and 2-chlorobenzal chloride.

The sum of the 2 fractions corresponded to a chemical yield of 92.2% of theory.

Example 3

Analogously to example 1, 305 parts by weight of o-chlorobenzyl chloride and 438.1 parts by weight of water were reacted with 876.3 parts by weight of dimethylamine at 140° C.

After aqueous workup as in example 1 and distillation at 50 mbar, the following fractions were obtained:

| Forerun: | bp = 114° C. | 9.6 parts by weight | purity: 99.6% |
| Main fraction: | bp = 117° C. | 259.1 parts by weight | purity: 99.9% |
| Bottom fraction: | | 38.3 parts by weight | purity: 96.7% |

According to HPLC, the main fraction did not contain any detectable proportions of bis(2-chlorobenzyl)dimethylammonium chloride and 2-chlorobenzal chloride.

The sum of the 2 fractions corresponded to a chemical yield of 95.4% of theory.

Example 4

Analogously to example 1, 76.24 parts by weight of o-chlorobenzyl chloride and 117.4 parts by weight of water were reacted with 228.2 parts by weight of dimethylamine at 170° C.

After aqueous workup as in example 1 and distillation at 14 mbar, the following fractions were obtained:

| Forerun: | bp = 84° C. | 1.6 parts by weight | purity: 99.1% |
| Main fraction: | bp = 84° C. | 71.5 parts by weight | purity: 99.2% |
| Bottom fraction: | | 2.0 parts by weight | purity: 88.9% |

According to HPLC, the main fraction did not contain any detectable proportions of bis(2-chlorobenzyl)dimethylammonium chloride and 2-chlorobenzal chloride.

The sum of the 2 fractions corresponded to a chemical yield of 92.8% of theory.

Example 5

The experiment of example 3 was repeated. Before the distillation, 33.4 parts by weight of distillation residue from example 3 were added.

After distillation at 50 mbar, the following fractions are obtained:

| Forerun: | bp = 108-116° C. | 27.9 parts by weight | purity: 97.6% |
| Main fraction: | bp = 116° C. | 299.7 parts by weight | purity: 99.2% |
| Bottom fraction: | | 15.6 parts by weight | purity: 86.2% |

According to HPLC, the main fraction did not contain any detectable proportions of bis(2-chlorobenzyl)dimethylammonium chloride and 2-chlorobenzal chloride.

Example 6

The following reactant streams were supplied by means of pumps to a reaction tube of 4.80 m length and 2 mm diameter, which had been provided with a pressure-retaining valve:

76.33 g/h of o-chlorobenzyl chloride
220.0 g/h of dimethylamine
110.0 g/h of water The dimethylamine and water streams were initially combined and preheated to 130° C. The stream of o-chlorobenzyl chloride was then introduced by way of a mixing chamber. The temperature in the reaction tube was set to approximately 140° C. After running through the reaction zone, the mixture was cooled and depressurized. The workup analogous to example 1 afforded the (2-chlorobenzyl)dimethylamine target product with a yield and purity as in example 3.

Example 7

144 parts by weight of a (2-chlorobenzyl)dimethylamine, which was prepared according to example 1 and still contained 0.1% by weight of o-chlorobenzaldehyde, were heated to 60° C. 0.27 parts by weight of sodium borohydride were then added and the mixture was further stirred for 3 h at 60° C.

HPLC analysis revealed that the content of o-chlorobenzaldehyde had decreased to 0.017% by weight.

The product was then distilled at 50 mbar. A water-containing forerun was removed, which was then reused in the next batch.

Forerun: bp=106° C., 14.4 parts by weight, purity: 99.4%, o-chlorobenzaldehyde content: 0.043%

Main fraction: bp=116° C., 93 parts by weight, purity: 99.0%, o-chlorobenzaldehyde content: 0.024%

Bottom fraction: 23.3 parts by weight, purity: 94.3%, o-chlorobenzaldehyde content: 0.034%

Comparative Example 8

The distillation of 317 parts by weight of a (2-chlorobenzyl)dimethylamine, which was prepared according to example 1, was carried out at 50 mbar without pretreatment according to example 7. The following fractions were obtained:

Forerun: bp=114° C., 9.6 parts by weight, purity: 99.5%, o-chlorobenzaldehyde content: 0.43%

Main fraction: bp=117° C., 259.1 parts by weight, purity: 99.9%, o-chlorobenzaldehyde content: 0.097%

Bottom fraction: 38.3 parts by weight, purity: 96.7%, o-chlorobenzaldehyde content: 0.23%

Example 9

Analogously to example 6, the reaction was carried out in a reaction tube of 42 m length and 0.7 mm diameter. The following reactant streams were used:
123 g/h of o-chorobenzyl choride
240 g/h of dimethylamine and
154 g/h of water.

Water and dimethylamine were combined outside the mixing chamber as in example 6 and preheated to 120° C. The reaction tube was operated for 29 h at 130° C. After depressurizing the dimethylamine, the reaction mixture was transferred to a 25 l stirred apparatus and slowly heated to 90° C. in order to outgas further dimethylamine. The mixture was further stirred for 1 h at 90° C. 4998 g of 50% aqueous sodium hydroxide solution was then added over 3.5 h at 90° C., whereupon further dimethylamine outgassed. The mixture was further stirred for 1 h at 90° C. At this temperature only the phases were separated, giving rise to 3647 g of organic phase. 1600 g of the organic phase above were processed by vacuum distillation at 200 mbar. The following fractions were obtained:

| | | | |
|---|---|---|---|
| Forerun: | bp = 59-151° C. | 13.6 g | purity: 75.6% |
| Main fraction: | bp = 152-153° C. | 1406 g | purity: 99.6% |
| Bottom fraction: | | 138.8 g | purity: 90.1% |

The sum of these fractions corresponds to a chemical yield of 93.8%

What is claimed is:

1. A method for preparing compounds of the formula (I)

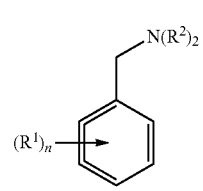

(I)

in which
n is 0, 1, 2 or 3
the residues $R^1$ are each independently a halogen atom bonded to the aromatic ring,
the residues $R^2$ are each independently $C_1$-$C_8$-alkyl, $C_6$-$C_{12}$-aryl or $C_7$-$C_{13}$-arylalkyl or both residues $R^2$ together are a straight-chain or branched $C_3$-$C_{12}$-alkylene residue, which may optionally be interspersed by one or more oxygen atoms,
the method comprising reacting compounds of the formula (II)

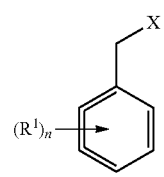

(II)

with compounds of the formula (III)

where the residues $R^1$ and $R^2$ in the formulae (III) and (II) have the meanings stated under the formula (I), and
X is chlorine, bromine, iodine, —$OSO_2$—($C_1$-$C_6$-alkyl) or —$OSO_2$—($C_1$-$C_6$-perfluoroalkyl)
wherein:
the molar ratio of compounds of the formula (III) to compounds of the formula (II) is 3:1 to 50:1;
organic solvent is optionally used in an amount of 0% to 10% by weight, based on the sum of compounds of the formulae (II) and (III) used;
water is used in the reaction in an amount of more than 10% by weight based on the amount of compound of the formula (II) used; and
the reaction is conducted at a temperature of 90° C. to 180° C.

2. The method as claimed in claim 1, wherein the method is a method for 2-chloro-N,N-dimethylbenzylamine by reacting 2-chlorobenzyl chloride with dimethylamine.

3. The method as claimed in claim 1 wherein:
the reaction temperature is 130 to 150° C.;
the reaction is conducted at a pressure of 5 to 35 bar;
n is 1, and $R^1$ and X are chlorine;

the molar ratio of compounds of the formula (III) to compounds of the formula (II) is 5:1 to 20:1;
no organic solvent is used; and
the amount of water used 100 to 1000%, by weight, based on the amount of compound of formula (II) used.

4. The method as claimed in any one of claims 1 to 3, further comprising conducting the reaction at a pressure of 2 to 300 bar.

5. The method as claimed in claim 1, wherein the method comprises conducting the reaction continuously.

6. The method for preparing compounds of the formula (I) as claimed in claim 1, wherein the prepared compounds of formula (I) after the method of claim 1 are in a mixture having a residual content of compounds of the formula (IV)

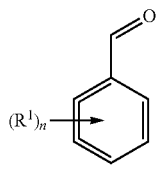

(IV)

in which $R^1$ has the meaning stated in claim 1 of 0.050 to 2.0% by weight and the method further comprises contacting the mixture with an alkali metal borohydride or an alkali metal aluminum hydride to react with the compounds of formula (IV); and subsequently separating compounds of formula (I) from the reacted compounds of formula (IV) by distillation.

7. The method as claimed in claim 6, wherein the method is a method for preparing 2-chloro-N,N-dimethylbenzylamine and the residual compound is 2-chlorobenzaldehyde.

8. The method as claimed in claim 6 or 7, wherein the alkali metal borohydride is sodium borohydride.

9. The method as claimed in claim 6, wherein the method of claim 6 is carried out subsequent to the method as claimed in claim 1.

10. A method for preparing compounds of the formula (V)

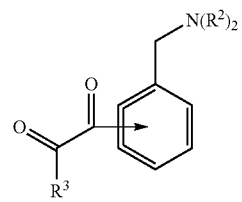

(V)

in which the residues $R^2$ are each independently $C_1$-$C_8$-alkyl, $C_6$-$C_{12}$-aryl or $C_7$-$C_{13}$-arylalkyl or both residues $R^2$ to together are a straight-chain or branched $C_3$-$C_{12}$-alkylene residue, which may optionally be interspersed by one or more oxygen atoms,
and $R^3$ is $C_1$-$C_6$-alkyl, $C_1$-$C_8$-alkoxy, $C_6$-$C_{12}$-aryl or $C_7$-$C_{13}$-arylalkyl,
the method comprising preparation of compounds of the formula (I) according to claim 1; reacting compounds of the formula (I), with an alkali metal or alkaline earth metal or a compound of the type M($C_1$-$C_6$-alkyl) where M is an alkali metal, and subsequently with compounds of the formula (VI)

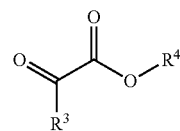

(VI)

in which the residue $R^3$ has the meaning stated for formula (V) and
$R^4$ is $C_1$-$C_8$-alkyl, $C_6$-$C_{12}$-aryl or $C_7$-$C_{13}$-arylalkyl.

* * * * *